US008530536B2

(12) United States Patent
Conzone et al.

(10) Patent No.: US 8,530,536 B2
(45) Date of Patent: Sep. 10, 2013

(54) SELF-LUBRICATING PHARMACEUTICAL SYRINGE STOPPERS

(75) Inventors: Samuel D. Conzone, Castleton, NY (US); David M. Rusinko, North Royalton, OH (US); Chandrashekar Raman, North Royalton, OH (US); Indumathi Ramakrishnan, Bangalore (IN); Anantharaman Dhanabalan, Bangalore (IN); Mayank Kumar Dubey, Bangalore (IN); Sumi Dinkar, Bangalore (IN); Mayanglambam Rebika Devi, Bangalore (IN); Markus Bley, Düsseldorf (DE)

(73) Assignee: Momentive Performance Materials Inc.

( * ) Notice: Subject to any disclaimer, the term of this patent is extended or adjusted under 35 U.S.C. 154(b) by 0 days.

(21) Appl. No.: 13/227,625

(22) Filed: Sep. 8, 2011

(65) Prior Publication Data

US 2012/0065595 A1    Mar. 15, 2012

Related U.S. Application Data

(63) Continuation-in-part of application No. 12/896,327, filed on Oct. 1, 2010.

(60) Provisional application No. 61/247,770, filed on Oct. 1, 2009.

(51) Int. Cl.
*C08J 5/16*    (2006.01)

(52) U.S. Cl.
USPC ................................. 522/75; 522/78

(58) Field of Classification Search
USPC ...................... 640/230; 523/75, 78
See application file for complete search history.

(56) References Cited

U.S. PATENT DOCUMENTS

| 4,760,116 | A | * | 7/1988 | Roberts .......................... 525/221 |
| 5,153,039 | A |   | 10/1992 | Porter et al. |
| 5,331,019 | A | * | 7/1994 | Payne et al. ..................... 522/75 |
| 5,356,948 | A | * | 10/1994 | Payne et al. ..................... 522/75 |
| 5,413,563 | A |   | 5/1995 | Basile et al. |
| 5,782,815 | A |   | 7/1998 | Yanai et al. |
| 6,027,481 | A |   | 2/2000 | Barrelle et al. |
| 6,296,893 | B2 | * | 10/2001 | Heinz et al. .................. 427/2.28 |
| 6,746,430 | B2 |   | 6/2004 | Lubrecht |
| 6,939,576 | B2 |   | 9/2005 | Deshpande et al. |
| 7,648,487 | B2 | * | 1/2010 | Ito et al. ......................... 604/230 |
| 2006/0200084 | A1 | * | 9/2006 | Ito et al. ........................ 604/230 |
| 2006/0264897 | A1 |   | 11/2006 | Lobl et al. |

(Continued)

OTHER PUBLICATIONS

U.S. Office Action dated Dec. 4, 2012, for U.S. Appl. No. 12/896,327.

(Continued)

*Primary Examiner* — James J Seidleck
*Assistant Examiner* — Peter A Salamon
(74) *Attorney, Agent, or Firm* — Joseph E. Waters

(57) ABSTRACT

In one aspect, a self-lubricating component is provided for a pharmaceutical packaging assembly. The self-lubricating component comprises a polymer composition and an effective amount of a lubricating additive such as, for example, boron nitride. In another aspect, a pharmaceutical packaging assembly may be provided having a surface thereof coated with a lubricating composition comprising boron nitride. The pharmaceutical packaging composition may be, for example, a pre-filled syringe comprising a body (barrel) and a plunger assembly.

19 Claims, 3 Drawing Sheets

(56) References Cited

U.S. PATENT DOCUMENTS

| | | | |
|---|---|---|---|
| 2008/0312111 A1 | 12/2008 | Malshe et al. | |
| 2009/0004231 A1* | 1/2009 | Popp ............................ | 424/400 |
| 2009/0209922 A1 | 8/2009 | Boisjoly | |
| 2011/0082430 A1 | 4/2011 | Conzone et al. | |

OTHER PUBLICATIONS

International Search Report for PCT/US2011/053845 dated Jan. 18, 2012.

Anderson et al, Biotech. App. Biochem, v32, pp. 145 (2000).

* cited by examiner

SELF-LUBRICATING PHARMACEUTICAL SYRINGE STOPPERS

CROSS REFERENCE TO RELATED APPLICATIONS

The present application claims priority as a continuation-in-part application to U.S. application Ser. No. 12/896,327, filed on Oct. 1, 2010, which claims priority to U.S. Provisional Patent Application No. 61/247,770, filed on Oct. 1, 2009, each of which is incorporated by reference herein in its entirety.

FIELD OF INVENTION

The present invention relates to components for a pharmaceutical packaging assembly and a pharmaceutical packaging assembly comprising such components. In particular, aspects of the present invention relate to self-lubricating components adapted for sliding engagement with an interior surface of a pharmaceutical packaging assembly, or a packaging assembly coated with a lubricious coating layer.

BACKGROUND

There has been a recent trend in the pharmaceutical market toward the use of pre-filled injectable syringes. These syringes provide benefits of requiring less overfill than traditional syringes, reduced needle-stick injuries, and less risk of cross-infection. Because of these benefits, many of the expensive biological (protein-based) drugs are delivered via pre-filled injectables. However, syringes, unlike ampoules and vials, require a layer of lubricant inside the syringe barrel to facilitate the easy movement of the plunger. As shown in FIG. 1, extractables from the lubricant as well as the packaging containers can cause poisoning and reduced efficacy of these drugs (see, e.g., U.S. Pat. Nos. 5,782,815 and 6,027,481).

FIG. 1 is a schematic illustration of a syringe and the presence of extractables from a lubricant coating from the syringe barrel in injectables of the syringe. FIG. 1 illustrates a syringe containing a drug/biotherapeutic 2 and having a lubricating silicone oil layer 4. The silicone oil droplet 6 leaches into the dispersion, and precipitates as a drug precipitate 8-oligomers on silicone oil droplets.

The lubricants are required to ensure smooth and steady injection of the drug, and to minimize the push force required to administer the drug, once the needle is embedded into the patient's skin. Lack of lubrication can result in non-steady, or excessive force to extract the drug from the container resulting in sudden movement of the needle embedded in the patient's skin leading to pain or injury.

In addition, oxygen and moisture permeation through rubber stoppers can cause denaturing of the drug. That is, protein denaturation due to oxidation is well established in the literature (Anderson et al, Biotech. App. Biochem, v 32, pp 145 (2000)). Ceramic fillers and other additives can be compounded with the polymer stoppers to reduce the oxygen and moisture permeation rates, thus minimizing denaturing due to exposure of the drug to these contaminants over time (see, e.g., U.S. Pat. No. 5,153,039).

The most widely used conventional lubricant for syringe stoppers is silicone oil. Challenges with silicone oil include (1) a high break-force due to migration of silicone oil from between the plunger and the tube during storage, and (2) interaction of the silicone oil with the biological drugs that results in agglomeration and denaturing, thus reducing drug efficacy. Some have addressed these issues by replacing the silicone oil with hard-baked silicone coatings, fluorocarbon films, and non-silicone coatings (e.g. TriboGlide®, which is based on perfluoropolyether chemistries). Although these coatings claim to address the break-force and denaturing issues, the addition of coatings into a manufacturing process adds cost and complexity.

Thus, a need exists for an effective lubrication alternative for stoppers in pharmaceutical applications.

SUMMARY

The present invention provides a pharmaceutical packaging assembly having one or more components moveable within a body of the assembly, wherein the one or more components exhibit excellent lubricity and stability without the side affects experienced with prior lubricated systems such as contamination of the packaging assembly's contents or "unwetting" of the packaging assembly body.

In one aspect, the present invention provides a self-lubricating component for use in pharmaceutical packaging assembly. The self lubricating component comprises a material comprising an effective amount of lubricating additive. Exemplary lubricating additives include boron nitride and PTFE.

In another aspect, the present invention provides a pharmaceutical packaging assembly comprising a barrel having an interior surface coated with a composition comprising a lubricating additive. The lubricating additive may include boron nitride. The pharmaceutical packaging assembly may further include a plunger, and the plunger may optionally be coated with a lubricating composition or may be formed from a self-lubricating material comprising a lubricating additive.

Aspects of the present invention may be further understood with reference to the following detailed description.

DETAILED DESCRIPTION

The present technology relates to a pharmaceutical packaging assembly having one or more components moveable within the assembly. In one embodiment, the pharmaceutical packaging assembly may be adapted for dispensing a liquid such as medicaments, pharmaceuticals, and the like. In one embodiment, the assembly is designed for the liquid or dry (lyophilized) storage of drugs. For example, the pharmaceutical packaging assembly may comprise a syringe, and, in embodiments, the syringe may be a pre-filled syringe.

Figure 1:
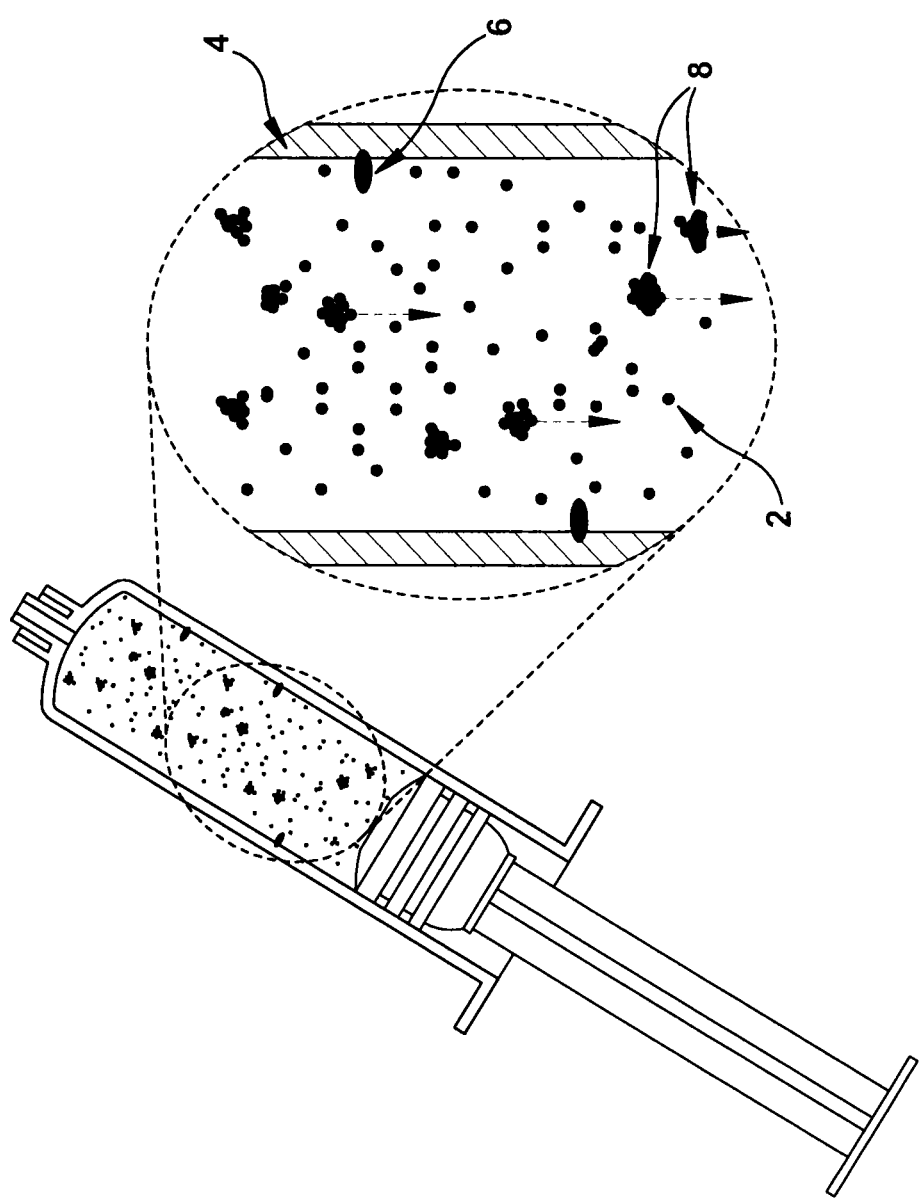
FIG. 1 is a schematic illustration of a syringe and the presence of extractables from a lubricant coating from the syringe barrel in injectables of the syringe.
Figure 2:
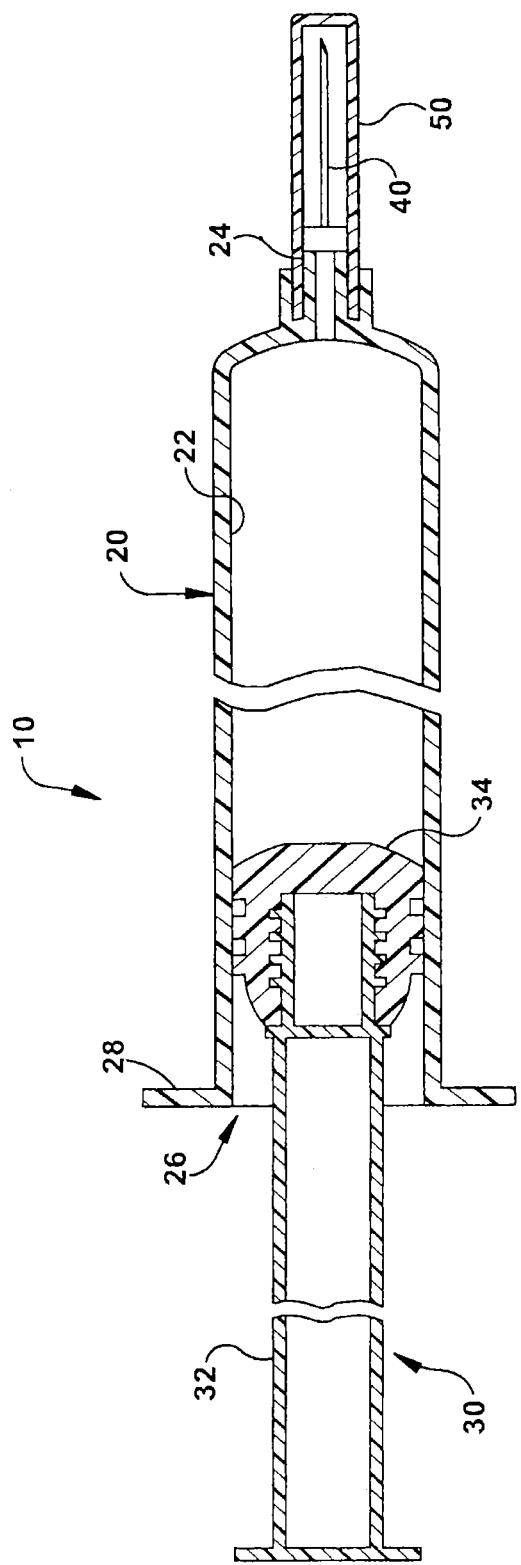
FIG. 2 is a cross section of a pre-filled syringe in accordance with aspects of the present invention.

Referring to FIG. 2, a non-limiting embodiment of a pharmaceutical packaging assembly 10 is shown in the form of a syringe (also referred to by numeral 10). The syringe 10 includes a body 20 for housing a fluid and a plunger assembly 30. The body 20 includes an inner wall or surface 22, a distal end terminating in a tapered tip 24, and a proximal end 26 for receiving the plunger assembly 30. Disposed about the periphery of the distal end 26 is flanged portion 28, which may also be referred to as a finger hub, to facilitate holding the body 20 during operation of the plunger. A needle assembly 40 is connected to the tip 24. The packaging assembly may further comprise a removable cover 50 disposed about the needle 40 and the tip 24 to protect the contents of the syringe prior to use, especially when provided as a pre-filled syringe.

The plunger assembly 30 includes a plunger rod 32 and a plunger 34. The plunger assembly is generally adapted to be slideably positioned in the body 20. The plunger assembly is typically sized to closely fit within the body 20 to reduce or eliminate leakage of a fluid housed in the body 20. The syringe may be operated by exerting a force on the plunger rod 32, which drives the plunger and forces the fluid housed in the body to be dispensed through the tip 24 and out the needle 40. The plunger 34, which may also be referred to herein as a stopper, may be formed from a material chosen from, for example, a rubber, a plastic, or a silicone material. The plunger rod 32 may be formed of any suitable material including a rubber, a plastic, a glass, or the like.

In accordance with aspects of the present invention, one or more of a portion of the body of the pharmaceutical package and a moveable component (such as the plunger/plunger assembly) of the packaging assembly is provided to exhibit sufficient lubricity for the moveable component to be suitably moveable within the packaging assembly body to perform its desired function (e.g., the sliding engagement of the plunger on the inner surface of the syringe body to force liquids out of the syringe). In one embodiment, a moveable component may be formed from a self-lubricating material to provide a self-lubricating component. Referring to FIG. 2, for example, an embodiment of the packaging assembly 10 may include a plunger 34 formed from a self-lubricating material. The self-lubricating material may comprise, for example, a self-lubricating rubber, plastic, or silicone comprising a lubricious additive or filler. Suitable lubricating additives or fillers include those from the following: Boron nitride, graphite, molybdenum disulfide, talc, mica, colloidal silica, fumed silica, high molecular weight silicone gum, Reimer's salt, siloxane particles (including, for example, methylsilsesquioxane micro-fine resin particles such as those sold under the tradename Tospearl), any salt, ester, or amide of a fatty acid, vinylfluoro silicones, D4, or combinations of two or more thereof. Boron nitride (BN) is an exemplary lubricating additive and provides excellent results. Examples of suitable salts, esters, or amides of fatty acids include, but are not limited to, zinc stearate, oleamide, erucamide, pentaerythritol stearate, and the like. A particularly suitable lubricating additive is hexagonal boron nitride (hBN). The lubricating filler provides self-lubricating properties to the plunger, thus eliminating the need to add lubricating coatings, such as silicone oil, baked silicone, or fluorocarbon coatings.

The amount of filler loading in the self-lubricating material may range from about 0.1 to 50% by weight. In one embodiment the filler loading is from about 3 to about 20% by weight. In another embodiment, the filler loading is from about 5 to about 10% by weight.

The base material for forming the self-lubricating material may be selected as desired. In the case of a polymer material, the polymer may be any conventional material suitable for use as a syringe plunger. Non-limiting, exemplary materials include natural rubber, silicone elastomers, thermoplastic elastomers, isobutylene or polybutadiene rubber, polytetrafluoroethylene, fluorosilicone rubbers, chlorinated polyethylene elastomers, ethylene vinyl acetate, hexafluoropropylene-vinylidene fluoride-tetrafluoroethylene terpolymers (e.g., materials sold under the tradename Fluorel and Viton), butyl rubbers, synthetic polyisoprene rubber, styrene-butadiene rubbers, tetrafluoroethylene propylene copolymers, thermoplastic-copolyesters, and the like. Methods for compounding the filler in the base material (e.g., a polymer material) may be any known in the art.

In another aspect, at least a portion of a surface of the pharmaceutical packaging assembly is coated with a filled polymeric coating composition comprising a lubricating additive. The lubricating additive may be chosen from materials including the following: Boron nitride, graphite, molybdenum disulfide, talc, mica, colloidal silica, fumed silica, high molecular weight silicone gum, Reimer's salt, siloxane particles (e.g., Tospearl), vinylfluoro silicones, D4, or combinations of two or more thereof. A particularly suitable filler is hBN.

Referring again to FIG. 2 for example, in one embodiment the inner surface 22 of the body 20 may be coated with the filled coating. In another embodiment, at least a portion of plunger assembly including the surface of the plunger rod 32 or the plunger 34 may be coated with the filled coating. It will also be appreciated that a packaging assembly could be provided comprising a body with an inner surface thereof coated with an filled coating, and a plunger formed from a self-lubricating material.

As previously described with respect to the self-lubricating material (as may be used with, for example, the plunger), the amount of lubricating additive (e.g., BN or others) in the coating may range from about 0.1 to about 50% by weight, from about 3 to about 20% by weight, and even from about 5 to about 10% by weight. The polymer may be any conventional material suitable for use as a syringe plunger. Non-limiting exemplary materials include silicone elastomers, thermoplastic elastomers, isobutylene or polybutadiene rubber, or polytetrafluoroethylene.

The body of the pharmaceutical package may be formed from any suitable material. Non-limiting examples of suitable materials include glass, cyclic olefin copolymers, polymethylpentene, polyethylene, polypropylene, polystyrene, acrylic and mehtacrylic polymers, and the like. The degree of transparency or opacity of the body may also be selected as desired.

Due to its hexagonal structure, hBN is extremely lubricious, with a coefficient of friction of 0.2. BN is an inert, non-toxic material, and is expected to have minimal or no adverse interactions with the biological drugs, making it an excellent choice for the present embodiments.

Because the self-lubricating plunger is inherently lubricating, it is expected to have a minimal break-force, and will ensure a smooth and consistent actuation during drug delivery. Additionally, because of the excellent lubricating properties of boron nitride, the overall force required to depress the plunger and inject the drug will be reduced, thus minimizing the probability of injury and pain to the patient due to quick movements of the needle embedded into the patient's skin.

Further, adding BN powders to the polymeric resins should also reduce oxygen and moisture permeation rate. Similarly adding BN platelets to resins should have an added benefit of reducing the resin permeability. That is, it is known that adding platy/flaky talc powders to various resins (rubbers/elastomers and thermoplastics) will reduce permeability of oxygen through the resin.

In another aspect, BN polymeric coatings and composite coatings comprising boron nitride may be applied to a conventional syringe plunger and/or the syringe barrel wall in place of the traditional silicone oil coating for lubrication. Boron nitride coatings can be applied to either the tube or the plunger/stopper or both. Boron nitride coatings can be applied as a paint, or through various deposition processes such as chemical vapor deposition, plasma-enhanced chemical vapor deposition, chemical liquid deposition, ion-plasma deposition, physical vapor deposition, electron beam deposition, electroplating, etc.

Results

Figure 3:
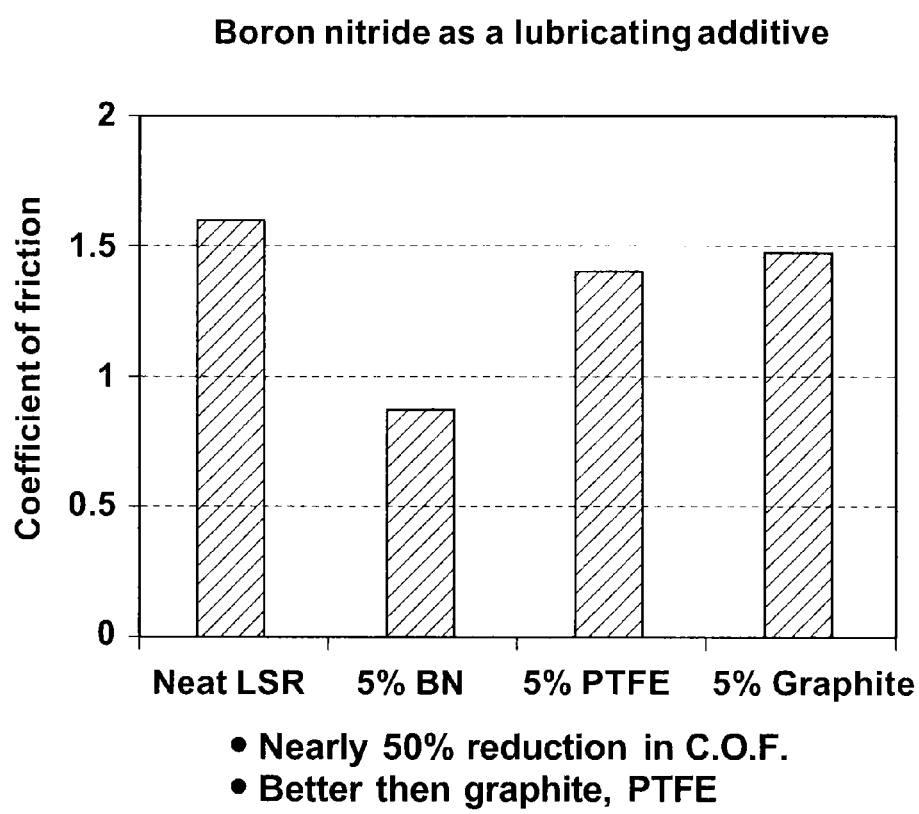
FIG. 3 is bar graph comparing the coefficient of friction of a silicone coating composition comprising different fillers.

Boron nitride, graphite, and PTFE fillers were compounded at 5 wt % into neat liquid silicone rubber "Neat LSR" silicone, and the coefficient of friction was measured on the resulting composites. As seen in FIG. 3, while all fillers showed some lubricating improvement over non-filled silicone, results showed that addition of hBN to the LSR reduced the coefficient of friction by approximately 50%, significantly better than that of the graphite and PTFE fillers.

While aspects of the invention have been described with respect to a syringe, it will be appreciated that the pharmaceutical package and the moveable component(s) are not limited to a syringe and a plunger, respectively. In addition to its use as a plunger in syringes, self-lubricating materials such as, for example, BN filled polymers, may find application where low friction forces are desired, and the use of an inert, immobile lubricant system is appropriate. The following is a partial list:

Barrel Syringe Manufacturing
Glass Syringe Lines for Prefilled Insulin
Glass Bottles & Specialty Chemistry Container s of High Value and/or Controlled Dose fluid can benefit from this technology.
Films that prevent wetting of the glass surface will reduce residual fluid in container.
Infusion Therapy
Contrast Media Market
Radioactive and Specialty Chemistries
Syringe Pump Components
Stoppers
Vial Coating
Electronic Leads & Contacts
Mechanical Valves, Ceramic Valves, Medical Valves
Mold Release Applications
Needle Lubrication
Catheter Lubrication
Plastic Threaded Components & Caps
Surgical Shields
Surgical Probes
Endoscope Lubrication
Elastomer Seals and/or Gaskets for Medical Devices
Surgical Cameras
Needle-free Access Valves Embodiments of the invention have been described above and modifications and alterations may occur to others upon the reading and understanding of this specification. The claims as follows are intended to include all modifications and alterations insofar as they come within the scope of the claims or the equivalent thereof.

What is claimed is:

1. A self-lubricating component for a pharmaceutical packaging assembly comprising a polymer composition comprising an effective amount of lubricating additive, wherein the lubricating additive comprises hexagonal boron nitride and wherein the component is in the form of a plunger, piston, diaphragm, or valve disc for medical equipment.

2. The component of claim 1 where the lubricating additive further comprises zinc stearate, oleamide, erucamide, pentaerythitol stearate or any salt, ester or amide of a fatty acid.

3. The component of claim 1, wherein the lubricating additive is present in an amount of from about 0.1 to about 50% by weight of the polymer composition.

4. The component of claim 1, wherein the lubricating additive is present in an amount of from about 3 to about 20% by weight of the polymer composition.

5. The component of claim 1, wherein the lubricating additive is present in an amount of from about 5 to about 10% by weight of the polymer composition.

6. A pharmaceutical package assembly comprising a barrel having an interior surface coated with a lubricating polymeric composition comprising a lubricating additive, wherein the lubricating additive comprises hexagonal boron nitride.

7. The pharmaceutical package assembly of claim 6, wherein the lubricating additive is present in an amount of from about 3 to about 20% by weight of the polymer composition.

8. The pharmaceutical package assembly of claim 6, wherein the lubricating additive is present in an amount of from about 5 to about 10% by weight of the polymer composition.

9. The pharmaceutical package assembly of claim 6 further comprising a plunger.

10. The pharmaceutical package assembly of claim 9, wherein the plunger is a self-lubricating component comprising a polymer composition comprising an effective amount of lubricating additive.

11. The pharmaceutical package assembly of claim 10, where the lubricating additive comprises one or more of: boron nitride, graphite, molybdenum disulfide, talc, mica, colloidal silica, fumed silica, high molecular weight silicone gum, Reimer's salt, siloxane particles, vinylfluoro silicones, D4, a salt, ester, or amide of a fatty acid, or any combination of two or more thereof.

12. The pharmaceutical package assembly of claim 9, wherein at least a portion of a surface of the plunger is coated with a lubricating polymeric composition comprising a lubricating additive.

13. A pharmaceutical package assembly comprising a plunger having at least part of its surface coated with a lubricating polymeric composition comprising a lubricating additive, where the lubricating additive comprises hexagonal boron nitride.

14. The package assembly of claim 13, wherein the lubricating additive is present in an amount of from about 0.1 to about 50% by weight of the polymer composition.

15. The package assembly of claim 13, wherein the lubricating additive is present in an amount of from about 3 to about 20% by weight of the polymer composition.

16. The package assembly of claim 13, wherein the lubricating additive is present in an amount of from about 5 to about 10% by weight of the polymer composition.

17. The component of claim 1, wherein the lubricating additive further comprises one or more of: boron nitride, graphite, molybdenum disulfide, talc, mica, colloidal silica, fumed silica, high molecular weight silicone gum, Reimer's salt, siloxane particles, a salt, ester, or amide of a fatty acid, vinylfluoro silicones, D4 or any combination of two or more thereof.

18. The pharmaceutical package assembly of claim 6, wherein the lubricating additive is chosen from one or more of: boron nitride, graphite, molybdenum disulfide, talc, mica, colloidal silica, fumed silica, high molecular weight silicone gum, Reimer's salt, siloxane particles, a salt, ester, or amide of a fatty acid, vinylfluoro silicones, D4 or any combination of two or more thereof.

19. The pharmaceutical package assembly of claim 13, wherein the lubricating additive is chosen from one or more of: boron nitride, graphite, molybdenum disulfide, talc, mica, colloidal silica, fumed silica, high molecular weight silicone gum, Reimer's salt, siloxane particles, a salt, ester, or amide of a fatty acid, vinylfluoro silicones, D4 or any combination of two or more thereof.

* * * * *